United States Patent [19]

Durant et al.

[11] Patent Number: 5,380,858
[45] Date of Patent: Jan. 10, 1995

[54] PROCESS FOR THE PREPARATION OF INTERMEDIATES USEFUL FOR THE SYNTHESIS OF HISTAMINE RECEPTOR ANTAGONISTS

[75] Inventors: Graham J. Durant; Amin M. Khan, both of Toledo, Ohio

[73] Assignee: The University of Toledo, Toledo, Ohio

[21] Appl. No.: 862,658

[22] Filed: Apr. 1, 1992

[51] Int. Cl.$^6$ ............................................. C07D 401/04
[52] U.S. Cl. ..................................................... 546/278
[58] Field of Search ........................................ 546/278

[56] References Cited

PUBLICATIONS

Bredereck et al., Chem. Berichte, 1953, 86, pp. 88–96.
Barlin et al., Aust. J. Chem., 1989, 42(10), pp. 1735–1748.
Chem. Abstracts. vol. 103 22520S (1985).

*Primary Examiner*—Marianne M. Cintins
*Assistant Examiner*—Phyllis G. Spivack
*Attorney, Agent, or Firm*—Pennie & Edmonds

[57] ABSTRACT

The present invention relates to a novel process for the preparation of highly potent histamine receptor antagonists, in particular histamine H$_3$receptor antagonists. Also disclosed is a novel process for the preparation of intermediates useful in the preparation of histamine receptor antagonists, in particular H$_3$-receptor antagonists.

9 Claims, No Drawings

PROCESS FOR THE PREPARATION OF INTERMEDIATES USEFUL FOR THE SYNTHESIS OF HISTAMINE RECEPTOR ANTAGONISTS

FIELD OF THE INVENTION

The present invention relates to a novel process for the preparation of intermediates useful in the synthesis of histamine receptor antagonists, in particular histamine $H_3$-receptor antagonists.

BACKGROUND OF THE INVENTION

Histamine receptor pharmacology has revealed three subtypes of receptors which mediate (or are associated with) the activity of histamine. These receptors are most commonly referred to as $H_1$, $H_2$, and $H_3$. The most recently discovered of these receptors is the $H_3$-histamine receptor. Early studies suggested the presence of another histamine receptor when it was demonstrated that histamine inhibits its own synthesis and release in brain slices by a negative feedback process operating at the level of histaminergic nerve-endings (see, for example, Arrang, J. M. et al. Nature 302:832–837 (1983)). More recently, the $H_3$-receptor has been shown to function as a pre-synaptic autoreceptor inhibiting histamine synthesis and histamine release from neurons, especially in the control nervous system (Arrang, et al. Nature 327:117–123 (1987)). The presence of $H_3$-receptors in peripheral tissues has also been reported and here too they appear to be involved with the nervous system. Thus, histamine depresses sympathetic neurotransmission in the guinea pig mesenteric artery by interacting with $H_3$-receptors on the perivascular nerve terminals (Ishikawa and Sperelakis, Nature 327:158 (1987)). This important observation suggests that histamine may control tile release of other neurotransmitters (Tamura et al., Neuroscience 25:171 (1988)). Inhibitory histamine $H_3$-receptors also exist in the guinea pig ileum where their role appears to be to modify the magnitude of histamine contraction, rather than affecting histamine release (Trzeciakowski, J. Pharmacol. Exp. Therapy 243:847 (1987)). Particularly intriguing is the discovery of $H_3$-receptors in the lung (Arrang et al. Nature 327: 117–123 (1987)). The presence of histamine $H_3$-receptors in the lung raises the question of whether they control histamine release in anaphylaxis and whether they may be manipulated to provide therapy in asthma. Indeed it has been suggested that $H_3$-receptors may have a modulating role on excitatory neurotransmission in airways. Generally, however, $H_3$-receptor inhibition tends to increase histamine activity, with potentially detrimental effects. Thus, it is desirable to avoid introducing $H_3$-receptor antagonists that act on peripheral tissues.

Histamine $H_3$-receptor activation was found to inhibit acetylcholine release in a guinea pig ileum model (Poli et al., Agents and Actions 33: 167–169). Selective $H_3$-receptor blockers reversed the histamine-induced inhibitory effect. Histamine also decreased serotonin release; this effect was reversed with an $H_3$-antagonist, and was suggested to operate via the histamine $H_3$-receptors (Schlicker et al., Naunyn-Schmiedaberg's Arch. Pharmacal. 337:588–590 (1988). Activation of $H_3$-receptors was found to inhibit excitatory presynaptic potentials (Arrang et al., (J. Neurochem. 51:105 (1988)).

One reported highly specific competitive antagonist of histamine $H_3$-receptors is thioperamide (Arrang et al., Nature 327:117–123 (1987)). Although thioperamide is a very potent antagonist in vitro ($K_i$= 4.3 nmol/L), relatively high doses are required in vivo to inhibit histamine release from the brain in rats (Ganellin et al., Collect. Czech. Chem. Commun. 56:2448–2455 (1991)). Ganellin et al. suggests that this most probably results from poor penetration through the blood-brain-barrier by this peramide, although the pharmacokinetic properties of thioperamide may also play a role. Moreover, the thiourea functionality found in thioperamide may result in higher intrinsic toxicity of thioperamide.

The previously described literature synthesis of 4-(4-pyridyl)-1H-imidazole is a lengthy procedure starting from 4-acetylpyridine. This procedure requires the conversion of 4-acetylpyridine into its oxime, followed by conversion to the O-tosylate, followed by rearrangement to an α-aminoketone using elemental potassium in ethanolic hydrogen chloride (G. R. Clemo, et al., J. Chem. Soc. (London 753 (1938)). The latter step is unattractive and potentially hazardous due to the flammability of potassium. The α-aminoketone is converted to the 2-mercaptoimidazole by treatment with potassium thiocyanate, and subsequent conversion (P. Neber et al., Liebigs Ann. Chem., 449: 109 (1926), 467: 52 (1928), 493:281 (1932)) to 4-(4-pyridyl)-imidazole is effected using concentrated nitric acid. This process leads to a very low yield of 4-(pyridyl)-imidazole.

4-Substituted piperdylimidazoles have been prepared by catalytic hydrogenation of the corresponding 4-pyridyl-imidazole. The 4-pyridyl-imidazole is obtained by reduction of the 2-mercaptoimidazole. (P. Neber, et al. Liebig Ann. Chem., 449: 109 (1926), 467: 52 (1928), 493: 281 (1932). Schunack, W., Archiv. Pharma. 306: 934 (1973)). Utility of this intermediate in the synthesis of known $H_3$-receptor antagonists, including thioperamide (Arrang, et al., Nature, 327: 117 (1987)) has been described by Arrang in U.S. Pat. No. 4,707,487 issued on Nov. 17, 1987 which discloses (4-imidazolyl)-piperidine derivatives that are useful to control the release of cerebral histamine and to increase the rate of renewal of cerebral histamine.

It is an object of the present invention to provide a novel process for the preparation of intermediates useful in the synthesis of novel histamine receptor antagonists, in particular histamine $H_3$-receptor antagonists.

It is a further object of the present invention to provide a novel process for the preparation of intermediates of known histamine receptor antagonists.

In addition, it is an object of the present invention to provide a process for the preparation of histamine receptor antagonists or their intermediates in high yield while using fewer steps than the prior art.

It is yet another object of the present invention to provide a novel process for the preparation of potent histamine receptor antagonists, in particular histamine $H_3$-receptor antagonists that are better able to penetrate the blood-brain-barrier than previously reported compounds and that have reduced toxicity compared to other known histamine antagonists.

SUMMARY OF THE INVENTION

The process of the present invention comprises activating the α-methyl group of a 2,3 or 4-acetyl-pyridine. The activated acetylpyridine is then reacted with formamide or a formamide derivative to yield an imidazole or substituted imidazole. Thereafter, the pyridyl moiety can be selectively reduced to afford piperidyl imidazoles.

The process of the invention is useful for preparing intermediates or starting materials for the synthesis of histamine receptor antagonists. In particular, the instant process can be used to produce 4-(piperidyl)-1H-imidazoles which are used in the preparation of histamine H3-receptor antagonists. The present invention also includes processes for preparing histamine H3-receptor antagonists from the 4-(piperidyl)-1H-imidazole intermediates.

DETAILED DESCRIPTION OF THE INVENTION

The present invention relates to a novel process for the preparation of a (2,3 or 4-imidazolyl)-pyridine of the Formula (3) and a (2,3 or 4-imidazolyl)-piperidine of the Formula (4)

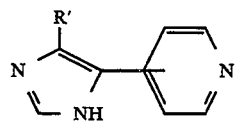

(3)

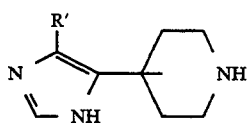

(4)

wherein R' is H or $C_1$-$C_4$ alkyl.

Also, the present invention relates to a novel process for the preparation of (4-imidazolyl)-piperidines of the Formula (I):

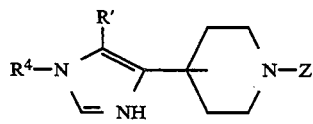

(I)

wherein R' is H or $C_1$-$C_4$ alkyl; $R_4$ is H,

or $C_1$-$C_4$ alkyl; and Z is

or $R^2$ and $R^1$, $R^2$, $R^4$, and $R^7$ are as defined below;

In one embodiment of the present invention, there is provided a method for the preparation of a compound of Formula (3):

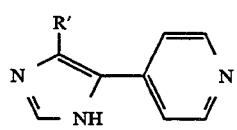

(3)

wherein R' is H or $C_1$-$C_4$ alkyl; which comprises:
(1) in a first step reacting a compound of the Formula (1)

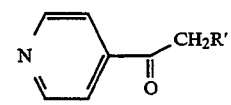

(1)

wherein R' is H or $C_1$-$C_4$ alkyl; with an activating reagent in a suitable solvent to produce an activated compound of the Formula (2a)

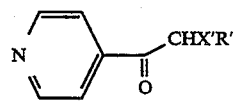

(2a)

where X' is halogen, hydroxy or amino and R' is H or $C_1$-$C_4$ alkyl; and (2) in a second step reacting a compound of the Formula (2a) with a compound of the Formula

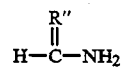

where R" is $NH_2$ or O at an elevated temperature to yield a compound of the Formula (3).

The activating reagent in step (1) is a compound capable of removing a hydrogen atom from the α-methyl group of (1) and replacing that hydrogen with a halogen, hydroxy or amino function. Preferably the activating reagent is selected from the group consisting of (1) a halogen, preferably bromine or chlorine, (2) molybdenum peroxide or (3) bromine or chlorine followed by hexamethylenetetramine. In compound 2(a), the group R' is hydrogen or a lower alkyl having 1 to 4 carbon atoms preferably methyl, and X' is a halogen, preferably bromine. When the activating reagent in step (1) is bromine, the preferred solvent is acetic acid.

In step (2), in the compound of the Formula

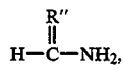

R" may either be NH or O and when R" is O, the reaction is preferably performed at a temperature between about 50°-to about 300° C. However, other temperatures can be used.

In a second embodiment, there is provided a method for the preparation of a compound of Formula (4):

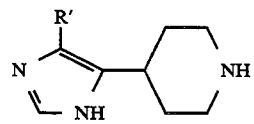

(4)

where R' is H or $C_1$-$C_4$ alkyl; which comprises:
(1) in a first step reacting a compound of the Formula (1)

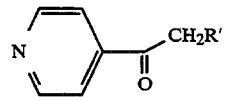

(1)

wherein R' is H or $C_1$–$C_4$ alkyl; with an activating reagent in a suitable solvent to produce an activated compound of the Formula (2a)

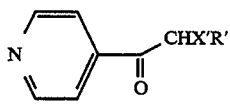
(2a)

where X' is halogen, hydroxy or amino and R' is H or $C_1$–$C_4$ alkyl; and (2) in a second step, reacting a compound of the Formula (2a) with a compound of the Formula

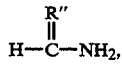

wherein R" is as defined above, preferably at an elevated temperature, to yield a compound of the Formula (3) and

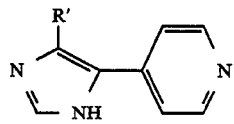
(3)

(3) in a third step, reacting a compound of Formula (3) with hydrogen in the presence of a noble metal catalyst at a suitable pressure in a suitable solvent to yield a compound of Formula (4).

The activating reagent in step (1) is a compound capable of removing a hydrogen atom from the α-methyl group of (1) and replacing that hydrogen with a halogen, hydroxy or amino function. Preferably the activating reagent is selected from the group consisting of (1) a halogen, preferably bromine or chlorine, (2) molybdenum peroxide or (3) bromine or chlorine followed by hexamethylenetetramine. In compound 2(a) the group R' is a hydrogen or a lower alkyl having 1 to 4 carbon atoms, preferably methyl and X' is a halogen, preferably bromine. When the activating reagent in step (1) is bromine, the preferred solvent is acetic acid. However, other solvents such as tetrahydrofuran may be used.

In step (2), R" may either be NH or O and when R" is O, the reaction is preferably performed at a temperature between about 50°–to about 300° C. However, other temperatures can be used.

In step (3), a noble metal catalyst is utilized. Preferably the noble metal catalyst is about 5% to about 10% rhodium on carbon. A suitable pressure is from about 20 to about 300 atmospheres. The preferred pressure is about 20 to about 100 atmospheres. A suitable solvent as defined previously is used. Suitable solvents include but are not limited to acidified water, lower alcohols, toluene and acetone. A preferred solvent is acidified water.

In a third embodiment, there is provided a method for the preparation of compounds of the Formula (I):

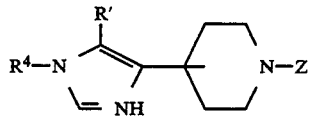
(I)

wherein R' is H or $C_1$–$C_4$ alkyl and $R_4$ is H,

or which comprises: $C_1$–$C_4$ alkyl; Z is as defined below; which comprises:

(1) in a first step reacting a compound of the Formula (1)

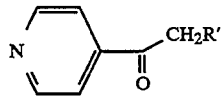
(1)

wherein R' is H or $C_1$–$C_4$ alkyl; with an activating reagent in a suitable solvent to produce an activated compound of the Formula (2a)

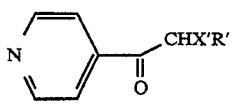
(2a)

where X' is halogen, hydroxy or amino and R' is H or $C_1$–$C_4$ alkyl; and (2) in a second step reacting a compound of the Formula (2a) with a compound of the Formula

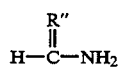

where R" is NH or O at an elevated temperature to yield a compound of the Formula (3);

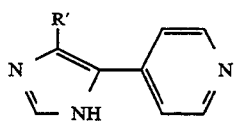
(3)

wherein R' is H or $C_1$–$C_4$ alkyl; and in a third step, reacting a compound of Formula (3) with hydrogen in the presence of a noble metal catalyst at a suitable pressure in a suitable solvent to yield a compound of Formula (4);

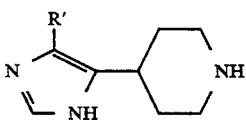
(4)

wherein R' is H or $C_1$–$C_4$ alkyl; and (4) in a fourth step, reacting a compound of Formula (4) with
  (a) the appropriate acid chloride in the presence of an organic base in an aprotic, organic solvent; or
  (b) the appropriate anhydride or carbonate in the presence of an organic base; or
  (c) an isocyanate of the Formula O=C=N—$R^7$ where $R^7$ is as defined below; or
  (d) isothiocyanate of the Formula S=C=N—$R^7$ where $R^7$ is as defined below to yield the compound of the Formula (I);

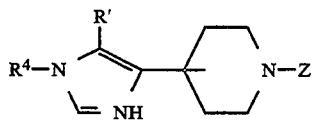 (I)

wherein
Z is

or $R^2$;

$R'$ is H or $C_1$-$C_4$ alkyl;

$R^1$ is $OR^2$, $(CH_2)_nR^3$, $C_1$-$C_{20}$ alkyl, $C_1$-$C_{20}$ alkenyl, $C_1$-$C_{20}$ cycloalkyl, $C_1$-$C_{20}$ cycloalkenyl and $C_1$-$C_2$ alkylaryl;

$R^2$ is $C_1$-$C_6$ alkyl, piperonyl or $(CH_2)_nR^3$;

$R^3$ is adamantyl methyl, $C_1$-$C_{20}$cycloalkyl, $C_1$-$C_{20}$ cycloalkyl phenyl methylene, $C_1$-$C_{20}$ dicycloalkyl methylene, diphenyl methylene, Y—$C_6$-$H_4$—$R^5$ or

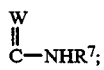

$R^4$ is H,

or $C_1$-$C_4$ alkyl;

$R^5$ is H, $CH_3$, halogen, CN, $CF_3$ or $COR^6$;

$R^6$ is $C_{1-C20}$ linear or branched chain alkyl, $C_1C_{20}$ cycloalkyl, phenyl or phenyl substituted with 1-3 substituents selected from the group consisting of $CH_3$ or F;

$R^7$ is $C_1$-$C_{20}$ linear or branched chain alkyl, $C_1$-$C_{20}$ cycloalkyl phenyl methylene, $C_1$-$C_{20}$ cycloalkyl alkyl methylene, $C_1$-$C_{20}$ dicycloalkyl methylene, phenyl, phenyl substituted with 1-3 substituents selected from the group consisting of $CH_3$, halogen, $CF_3$, $C_1$-$C_3$ alkyl (linear or branched);

X is S or O;

Y is a single bond or alternatively —O—, —S—, —NH—, —CO—, —CH=CH— or

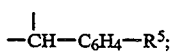

W is O S, NH, $NCH_3$ or NCN; and n=0-10.

The activating reagent in step (1) is a compound capable of removing a hydrogen atom from the α-methyl group of (1) and replacing that hydrogen with a halogen, hydroxy or amino function. Preferably the activating reagent is selected from the group consisting of (1) bromine or chlorine, (2) molybdenum peroxide or (3) bromine or chlorine followed by hexamethylenetetramine. In compound 2(a) the group R' is a hydrogen or a lower alkyl having 1 to 4 carbon atoms, preferably methyl, and X' is a halogen preferably bromine. When the activating reagent in step (1) is bromine, the preferred solvent is acetic acid.

In step (2), in the compound of the formula

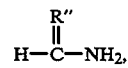

R" may either be NH or O and when R" is O, the reaction is preferably performed at a temperature between about 50° to about 300° C. However, other temperatures can be used.

In step (3), a noble metal catalyst is utilized. Suitable noble metal catalysts are as previously defined. Preferred noble metal catalysts include but are not limited to platinum or platinum oxide. The most preferred noble metal catalyst is 5%-10% rhodium on carbon. A suitable pressure is about 20 to about 300 atmospheres. The preferred pressure is from about 20 to about 100 atmospheres. A suitable solvent, as defined previously, is used. Suitable solvents include but are not limited to lower alcohols, acidified water, toluene and acetone. A preferred solvent is acidified water.

In step (4)(a) a suitable organic base is used. A preferred organic base is dicyclohexylamine. A suitable aprotic organic solvent may be used. The preferred aprotic organic solvent is acetonitrile. Preferably this reaction is carried out at room temperature, however, other temperatures can be used. Also, in step (4) (b) the organic base may be any of those used in step (4) (a). In addition, a preferred organic base to be used in step 4(b) is triethylamine.

In a forth embodiment, there is provided a method for the preparation of compounds of the Formula (I):

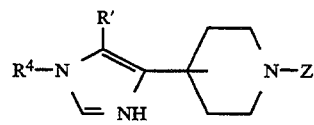 (I)

wherein R' R4 and 2 are as defined above; which comprises:

(1) in a first step reacting a compound of the Formula (1) with

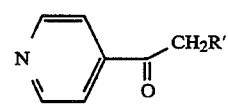

wherein R' is H or $C_1$-$C_4$ alkyl; an activating reagent in a suitable solvent to produce an activated compound of the Formula (2a)

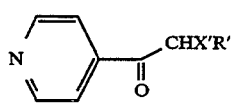 (2a)

where X' is halogen, hydroxy or amino and R' is H or $C_1$-$C_4$ alkyl; and (2) in a second step reacting a compound of the Formula (2a) with a compound of the formula

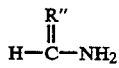

where R″ is NH or O; at preferably an elevated temperature to yield a compound of the Formula (3)

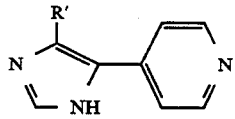
(3)

wherein R′ is as defined above; and (3) in a third step reacting a compound of Formula (3) with hydrogen in the presence of a noble metal catalyst at a suitable pressure in a suitable solvent to yield a compound of Formula (4)

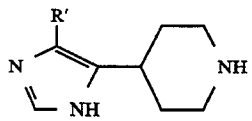
(4)

wherein R′ is as defined above; and (4) in a fourth step reacting a compound of Formula (4) with
  (a) the appropriate acid chloride in the presence of an organic base in an aprotic, organic solvent; or
  (b) the appropriate anhydride or carbonate in the presence of an organic base to yield the compound of the Formula (I) wherein Z is

or $R^2$;

$R^1$ is $OR^2(CH_2)_nR^3$, $C_1$-$C_{20}$ alkyl, $C_1$-$C_{20}$ alkenyl, $C_1$-$C_{20}$ cycloalkyl, $C_1$-$C_{20}$ cycloalkenyl and $C_1$-$C_{20}$ alkylaryl;

$R^2$ is $C_1$-$C_4$ alkyl or $(CH_2)_nR^3$;

$R^3$ is phenyl, adamantyl methyl, cycloalkyl of 1–10 carbon atoms, phenyl cyclohexyl methylene, dicyclohexyl methylene and $C_1$-$C_4$ alkyl;

$R^4$ is H;

X is O; and n=0–10; or (c) reacting the product of steps (a) or (b) with a base and alkylating the resultant anion with the appropriate alkyl halide to yield a compound of the Formula (I) where X is O and $R^4$ is $C_1$-$C_4$ alkyl; or (d) reacting the product of steps (a) and (b) or steps (a), (b) and (c) with a suitable reagent to yield a compound of the Formula (I) where X is S.

The activating reagent in step (1) is a compound capable of removing a hydrogen atom from the α-methyl group of (1) and replacing that hydrogen with a halogen, hydroxy or amino function. Preferably the activating reagent is selected from the group consisting of (1) bromine or chlorine, (2) molybdenum peroxide or (3) bromine or chlorine followed by hexamethylenetetramine. In compound 2(a) the group R′ is hydrogen or a lower alkyl having 1 to 4 carbon atoms, preferably methyl, and X′ is a halogen preferably bromine. When the activating reagent in step (1) is bromine, the preferred solvent is acetic acid.

In step (2), in the compound of formula

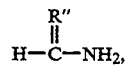

R″ may either be NH or O and when R″ is O, the reaction is preferably performed at a temperature of about 50° to about 300° C. However, other temperatures can be used.

In step (3), a noble metal catalyst is utilized. Preferably the noble metal catalyst is 5%–10% rhodium on carbon. A suitable pressure is from about 20 to about 300 atmospheres. The preferred pressure is from about 20 to about 100 atmospheres. Any suitable solvent, as defined herein, may be used. A preferred solvent is acidified water.

In step (4) (a) the organic base used is as defined herein. Preferably the organic base is a secondary amine. A most preferred organic base is dicyclohexylamine. A suitable aprotic organic solvent, as defined herein, may be used. The preferred aprotic organic solvent is acetonitrile. Preferably, the reaction is carried out at room temperature. However, other temperatures can be used. Also, in step (4) (b) the organic base may be any of those as defined herein. Preferably the organic base is a tertiary amine. In addition, a preferred organic base to be used in step 4 (b) is triethylamine.

In step (4) (c), a metal hydride base may be used. Preferred metal hydride bases are potassium or sodium hydride. The most preferred metal hydride base is sodium hydride. In step (4)(d), the introduction of a sulfur atom may be accomplished using compounds such as [2,4-bis(4-methoxyphenyl)-1,3-dithia-2,4-diphosphetane-2,4-disulfide]or phosphorus pentasulfide. Preferably phosphorus pentasulfide is used.

In a preferred embodiment of the process for the preparation of compounds of Formula (I) described herein, compounds of Formula (I) are prepared wherein:

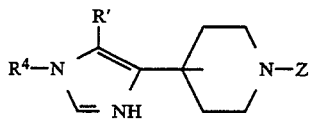
(I)

Z is

or $R^2$;

R′ is H;

$R^1$ is $OR^2$, $(CH_2)_nR^3$, $C_1$-$C_{20}$ alkyl, $C_1$-$C20$ alkenyl, $C_1$-$C_{20}$ cycloalkyl, $C_1$-$C_{20}$ cycloalkenyl and $C_1$-$C_{20}$ alkylaryl;

$R^2$ is $C_1$-$C_6$ alkyl or $(CH_2)_nR^3$;

$R^3$ is phenyl, adamantyl methyl, cycloalkyl of 1–10 carbon atoms, phenyl cyclohexyl methylene, dicyclohexyl methylene and $C_1$-$C_4$ alkyl;

$R^4$ is H, a hydrolyzable group and $C_1$-$C_7$ alkyl;

X is S or O; and n=0–10.

In a more preferred embodiment of the process for the preparation of compounds of Formula (I) described herein, compounds of the Formula (I) are prepared wherein:

$R^1$ is $OR^2$, $(CH_2)_nR^3$, $C_1$-$C_{20}$ alkyl and $C_1$-$C_{20}$ cycloalkyl;

$R^3$ is cyclopentyl, cyclohexyl, adamantyl methyl, dicyclohexylmethylene, phenyl and phenyl cyclohexyl methylene;

$R^4$ is H;

X is O; and n=3-6.

In a most preferred embodiment of the process described herein, those compounds of Formula (I) where:

$R^1$ is $OR^2$ or $(CH^2)_nR^3$; and n=4.

In specific preferred embodiments of the process described herein are the following compounds of the Formula (I) are prepared:

(a) 4-(1-Cyclohexylbutylcarbonyl-4-piperidyl)-1H-imidazole (b) 4-(1-Cyclohexylpropylcarbonyl-4-piperidyl)-1H-imidazole (c) 4-(1-Phenylethylcarbonyl-4-piperidyl)-1H-imidazole.

In a preferred embodiment of the present invention, commercially available 4-acetyl-pyridine (1) (Aldrich Chemical Co.) is converted into the key intermediate 4-(4-pyridyl)-1H-imidazole (3) by bromination of (1) with hydrogen bromide in acetic acid (Barlin, G. G. et al., Aust. J. Chem. 42: (1) 735 (1989)) to yield the bromacetyl pyridine (2) in high yield.

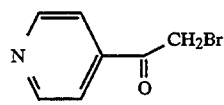

However, activation of the α-position of the ketone (1) may be effected with a variety of reagents including but not limited to (1) a halogen, preferably bromine or chlorine, (2) molybdenum peroxide or (3) bromine or chlorine followed by hexamethylene tetramine. Such reagents produce compounds where the α-methyl group bears a halide, hydroxy or amino group. For compounds where the activating group is a halide, treatment of (1) with bromine or chlorine yields the α-halo ketone. The α-halo ketone may be transformed to an α-amino ketone by treatment with hexamethylenetetramine. (Blazevic, et al., Synthesis, 161-176 (1979).

For compounds where the activating group is hydroxyl, the 4-acetyl-pyridine (1) may be treated with lithium diisopropylamide to produce an enolate which is subsequently treated with a molybdenum peroxide reagent (MoO5-pyridine-hexamethylphosphorustriamide) to yield the α-hydroxy ketone (E. Vedejs, J. Am. Chem. Soc., 96, 5944 (1974).

Reaction of (2) with formamide at about 110° C. affords the substituted imidazole (3) in high yield. The reaction is usually performed without the addition of any solvent. The synthesis of imidazoles not bearing a pyridyl substituent has been achieved from α-halo ketones using formamide (Brederich, H., et al., Chem. Berichte, 86:88 (1953)).

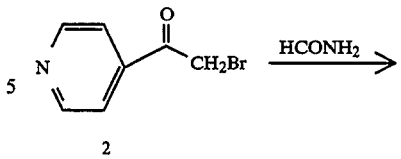

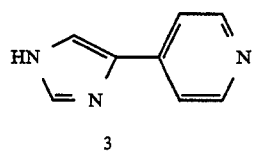

If desired, the process can be continued such that the pyridyl moiety of (3) is reduced by catalytic hydrogenation preferably using 5-10% Rhodium on carbon in acidified water at a pressure of about 20-about 55 atmospheres to yield (4). Selective reduction of the pyridine ring can also be accomplished with a variety of noble metal catalysts via hydrogenation methods well known to those skilled in the art. (V. Baliah, Chem. Rev., 83: 379-423 (1983)).

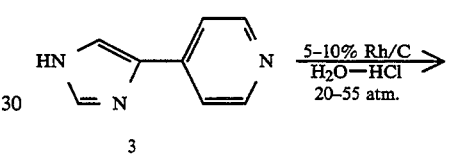

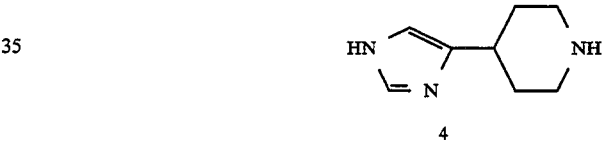

If desired, the (4-imidazolyl)-piperidine (4) can then be alkylated with the appropriate acid chloride (Method A) in acetonitrile at room temperature in the presence of dicyclohexylamine. The appropriate acid chloride can be prepared by reacting a carboxylic acid with sulfonyl chloride or optionally the appropriate acid chloride may be available commercially. The hydrochloric acid that is produced in this reaction is removed via salt formation with dicyclohexylamine to form dicyclohexylammonium chloride which precipitates and is removed from the reaction mixture by filtration. Via this method, compounds of the Formula (5) where Z is $COR^1$ may be produced. Alternatively, compounds of the Formula (5) where Z is $COR^1$ may be made via alkylation of (4) with the corresponding acid anhydride (Method B) in the presence of triethylamine. Compounds of the Formula (5) where Z is $COOR^2$ may be prepared via alkylation of (4) with the appropriate carbonate in the presence of triethylamine (Method B).

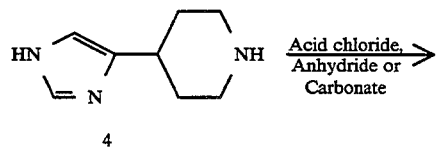

-continued

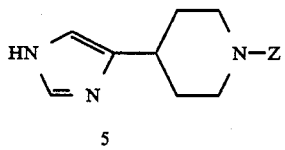

Compounds of the Formula (I) described previously, where R⁴ is other than hydrogen may be prepared by contacting a compound of the Formula I, where R⁴ is hydrogen, with a metal hydride such as sodium hydride and alkylating the corresponding anion with an alkyl halide in tetrahydrofuran at low temperatures from about −78° C. to about 0° C.

Compounds of the Formula (I) where R³ is

may be prepared by reacting a compound of the Formula (4) with a derivative of the Formula W=C=N—R⁷ in which W and R⁷ have the same meaning as in Formula (I) and, where appropriate, partial thermal decomposition of the disubstituted derivative (I, R⁴=Z=R²) to obtain the corresponding monosubstituted derivative (I, R⁴=H).

The condensation reaction with the derivative of Formula W=C=N—R⁷ (in particular, isocyanate and isothio cyanate when W is O and S, respectfully) can be performed in a manner known to those skilled in the art, for example at temperatures ranging from about 80° C. to about 130° C. under reflux in a neutral solvent such as toluene.

The thermal decomposition of the disubstituted compounds (I, R⁴=Z=R²) can be performed by heating and sublimation at temperatures in general greater than about 200° C. and under reduced pressure.

Compounds of the invention where Z is R² may be prepared by reacting a compound of the Formula (4) with a halogenated derivative R²X. The reaction with the halogenated derivative R²X can be performed in a known manner known to those skilled in the art by heating the reaction mixture to temperature ranging from about 60° C. to about 180° C. in a polar solvent such as dimethylformamide and in the presence of an acceptor for acid such as an alkali metal carbonate or alkali earth metal carbonate.

Further, compounds of the Formula (I) where R' is C₁-C₄ alkyl may be prepared according to the method of Pyman (*J. Chem. Soc.* 99: 668 (1911)).

Compounds of the Formula (I) where X=S may be prepared from the corresponding ketone by treatment with phosphorus pentasulfide under standard conditions.

The compounds of Formula (I) are H₃-receptor antagonists that have therapeutic utility in the treatment of cognitive disorders, e.g. such as those associated with Alzheimer's disease. Compounds that can be synthesized by the processes disclosed in the present application include, but are not limited to, are disclosed more fully in copending application Ser. No. 862,657, filed by the instant inventors of even date herewith, entitled "HISTAMINE H₃-RECEPTOR ANTAGONISTS AND THERAPEUTIC USES THEREOF", which is specifically incorporated herein by reference in its entirety.

The term "activating reagent" as used in the present application means a reagent that will participate in the removal of a hydrogen atom from the α-methyl group of (1) and replace it with a functional group, including but not limited to halogen, hydroxy or amino. The preferred activating reagent may be selected from the group consisting of bromine, chlorine, molybdenum peroxide or bromine or chlorine followed by hexamethylenetetramine. The most preferred reagent is bromine.

The term "suitable solvent" as used in the present application means a solvent appropriate to the reagents and materials employed and suitable for the transformation being effected. Unless stated otherwise, the reactions are performed at temperatures between about −100° C. and about the boiling point of the solvent used, as appropriate for a reasonable rate of reaction and the stability of the reagents, solvents and products involved. "Suitable solvents" to be used in the process of the present invention include but are not limited to organic acids, acetone, toluene, etylene, benzene, lower (C₁-C₄) alcohols and acidified water. The preferred solvent for the introduction of bromine is acetic acid. The preferred solvents for hydrogenation of the pyridine ring are toluene, lower (C₁-C₄) alcohols, acetone and acidified water. A most preferred solvent is acidified water.

The term "elevated temperature" refers to a temperature range from about room temperature to about the boiling point of the particular solvent being utilized for the particular reaction being employed to effect the desired transformation.

The term "noble metal catalyst" refers to the group including but not limited to palladium on carbon, platinum on carbon, nickel (raney nickel), platinum oxide, rhodium on carbon and ruthenium oxide. A preferred catalyst for hydrogenation of the pyridine ring is rhodium on carbon. A most preferred catalyst is 5–10% rhodium on carbon.

The term "suitable pressure" as used in the present application means a pressure appropriate to the reagents and materials employed, and suitable for the transformation being effected. A pressure range of about 20-to about 300 atmospheres may be used in the hydrogenation step(s) in this invention. A preferred pressure range is about 20-to about 100 atmospheres.

The term "appropriate anhydride" as used in this invention refers to the "anhydride" appropriate to the reagents and materials employed, and suitable for the transformation to be effected. In some cases, functional groups on the starting materials may need to be protected by standard protecting groups reported in the chemical literature. Such protecting groups include methyl ethers to protect hydroxyl groups, ethylene ketals to protect ketones and acetals to protect aldehydes.

The term "appropriate acid chloride" as used in this invention refers to the "acid chloride" appropriate to the reagents and materials employed, and suitable for the transformation to be effected. In some cases, functional groups on the starting materials may need to be protected by standard protecting groups reported in the chemical literature. Such protecting groups include methyl ethers to protect hydroxyl groups, ethylene ketals to protect ketones and acetals to protect aldehydes.

The term "appropriate carbonate" as used in this invention refers to the "carbonate" appropriate to the reagents and materials employed, and suitable for the transformation to be effected. In some cases, functional groups on the starting materials may need to be protected by standard protecting groups reported in the chemical literature. Such protecting groups include methyl ethers to protect hydroxyl groups, ethylene ketals to protect ketones and acetals to protect aldehydes.

The term "organic base" as used herein is defined as any organic compound capable of deprotonating a selected compound of the present invention or forming a salt with an inorganic or organic acid. Preferred "organic bases" of the present invention are secondary and tertiary amines. A most preferred secondary amine is dicyclohexylamine and a most preferred tertiary amine is triethylamine.

The term "aprotic, organic solvent" as used in this invention means a non-aqueous solvent that acts neither as a proton acceptor nor as a proton donor with respect to the solute. Preferred aprotic, organic solvents to be used in the present invention include, but are not limited to dimethylformamide, acetonitrile, dimethyl sulfoxide, acetone, sulfur dioxide and hexamethylphosphoric triamide. A most preferred solvent is acetonitrile.

The compounds of the invention and their synthesis are further illustrated by the following examples. It will be apparent to those skilled in the art, that modification to the processes described in the following examples may be practiced without departing from the purpose and interest of this invention. All temperatures are in degrees centigrade and parts and percentages by weight.

EXAMPLE 1 (Method A).

Part A: 4-(4-Pyridyl)-1H-imidazole

A mixture of 11.23 g (4.00 mmol) ω-bromoacetyl pyridine and 3.98 ml (10.0 mmol) formamide were fused together at 110° C. with stirring for 4 h. The crude reaction mixture was then concentrated on the rotary evaporator to remove volatile matter. The residue was dissolved in 50 mL methanol and to this solution was added 100 mL anhydrous diethyl ether slowly with stirring which led to the formation of a brown precipitate. After stirring for another 0.5 h, the precipitate was filtered, washed with 50 mL anhydrous ether and dried. This solid residue was dissolved in 20 mL water and the aqueous solution was basified to pH 9 with sodium carbonate. To this solution was added 150 mL absolute ethanol slowly with stirring till a solid formed, which was filtered off. The filtrate was heated to boiling, then treated with activated carbon and filtered. The filtrate was concentrated on rotary evaporator to dryness. Yield: 3.36 g 58%; M.P.: 152° C. (decomposed); MS: m/e 145 (M+), $^1$H NMR (D$_2$O): imidazole H: δ7.80 (s, 1H) and 7.20 (s, 1H); pyridyl H: 8.10 (d, 2H), 7.17 (d, 2H).

Part B:
4-(1-Cyclohexylbutylcarbonyl-4-piperidyl)-1H-imidazole

To a mixture of 755 mg (5.00 mmol) 4-(4-piperidyl)-1-H-imidazole and 942 mg (5.20 mmol) of dicyclohexylamine in 10 ml anhydrous acetonitrile at 25° C. was slowly added 1.06 g (5.20 mmol) cyclohexanevaleroyl chloride in 2 ml dichloromethane. The acid chloride was added over a period of ten minutes and then heated at 60° C. for 1.5 hr. After cooling to ambient temperature, the solid obtained (dicyclohexylammonium chloride) was filtered off and the filtrate was concentrated in vacuo to remove acetonitrile. The resulting crude oil was crystallized with methanol: anhydrous diethyl ether to give 1.085 mg of analytically pure product as a yellow powder.

Yield: 68%; M.P.: 159° C.; MS: m/e=317 (M+); $^1$H NMR (CDCL$_3$): imidazole H: δ6 7.65 (s, 1H), 6.75 (s, 1H). cyclohexylbutyl;, 2.20 (m, 8H), 1.20 (m, 1H), piperidyl: 4.65 (d. 2H) 3.95 (d. 2H) 3.10 (d. 2H) 2.84 (m, 1H) 2.20 (m, 2H).

EXAMPLE 2 (Method B)

4-(t-Butoxy-carbonyl-4-piperidyl) 1H-imidazole (Method B.)

To a suspension of 224 mg (1.00) mmol) of 4-(4-piperidyl)-1H-imidazole dihydrochloride in 10 ml of methanol was added 202 mg (2.00 mmol) of triethylamine (the suspension turned to a clear solution) followed by dropwise addition of 218 mg (1.00 mmol) of di-t-butyl dicarbonate in 5 ml methanol over a period of 10 minutes. The reaction mixture was stirred at 25° C. for 6 h, at the end of which the volatile materials were removed in vacuo. The oily residue was partitioned between 50 ml chloroform and 25 ml water. The organic layer was washed with 50 ml brine solution, then dried over anhydrous sodium sulfate. After filtration and removal of solvent, a pale yellow oil was obtained. The oil was treated with a mixture of methanol: petroleum ether (10:90). The resulting mixture was agitated vigorously with a glass rod until a solid appeared. After filtration and drying, time desired product was obtained as a white power. Yield: 65%; M.P.: 198° C.; MS: m/e 251 (M+); $^1$H NMR (CDCl$_3$): imidazole H: δ7.60 (s, 1H) and 6.60 (s, 1H); piperidine H: δ4.20 (d, 2H), 2.80 (m, 4H), 2.20 (d, 2H), 1.60 (m, 1H), t-BOC H: 1.45 (s, 9H).

Separation of pure product is by Prep. TLC Silica Gel GF. 60 (2000 Microns) and the solvent of recrystallization is methanol: anhy, ether (20:80).

The compound of Examples 1 and 2 and compounds which were prepared following procedures analogous to those outlined above are shown in Table I.

TABLE I $$R^4-N\underset{N}{\overset{R'}{\diagdown}}\diagdown\diagup N-Z$$

| EX. | R$^4$, R' | Z | METHOD | M.P. | M.S. (m/e) |
|---|---|---|---|---|---|
| 1 | H | CO(CH$_2$)$_4$C$_6$H$_{11}$ | A | 159 | 317 |
| 2 | H | CO$_2$C(CH$_3$)$_3$ | B | 198 | 251 |
| 3$^a$ | H | COCH$_2$C$_6$H$_{11}$ | A | OIL | 275 |
| 4$^b$ | H | COCH$_2$C$_6$H$_5$ | A | OIL | 267 |
| 5$^c$ | H | CO(CH$_2$)$_3$C$_6$H$_5$ | A | OIL | 297 |
| 6$^d$ | H | CO(CH$_2$)$_2$C$_6$H$_{11}$ | A | OIL | 289 |
| 7$^e$ | H | CO(CH$_2$)$_2$C$_6$H$_5$ | A | OIL | 283 |
| 8$^f$ | H | CO(CH$_2$)-ADAMANTYL | A | 151 | 327 |
| 9$^g$ | H | COCH(C$_6$H$_{11}$)$_2$ | A | 148 | 357 |
| 10$^h$ | H | COCH=CH—C$_6$H$_5$ | A | OIL | 281 |
| 11$^i$ | H | COCH(C$_6$H$_{11}$)(C$_6$H$_5$) | A | OIL | 351 |
| 12$^j$ | H | CO(CH$_2$)$_3$C$_6$H$_{11}$ | A | 136 | 304 |
| 13$^k$ | H | COC$_6$H$_5$ | B | 180 | 255 |
| 14$^l$ | H | COC(CH$_3$)$_3$ | B | 185 | — |
| 15 | H | CO(CH$_2$)$_5$C$_6$H$_{11}$ | A,B | — | — |
| 16 | H | CO(CH$_2$)$_6$C$_6$H$_{11}$ | A,B | — | — |
| 17 | H | CO(CH$_2$)$_7$C$_6$H$_{11}$ | A,B | — | — |
| 18 | H | CO(CH$_2$)$_8$C$_6$H$_{11}$ | A,B | — | — |
| 19 | H | CO(CH$_2$)$_9$C$_6$H$_{11}$ | A,B | — | — |
| 20 | H | CO(CH$_2$)$_{10}$C$_6$H$_{11}$ | A,B | — | — |
| 21 | H | CO(CH$_2$)$_5$C$_6$H$_5$ | A,B | — | — |

TABLE I-continued

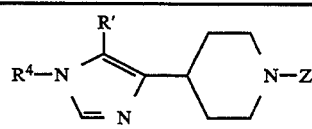

| EX. | R4, R' | Z | METHOD | M.P. | M.S. (m/e) |
|---|---|---|---|---|---|
| 22 | H | CO(CH2)6C6H5 | A,B | — | — |
| 23 | H | CO(CH2)7C6H5 | A,B | — | — |
| 24 | H | CO(CH2)8C6H5 | A,B | — | — |
| 25 | H | CO(CH2)9C6H5 | A,B | — | — |
| 26 | H | CO(CH2)10C6H5 | A,B | — | — |
| 27 | H | CO(CH2)2CH(C6H11)2 | A,B | — | — |
| 28 | H | CO(CH2)3CH(C6H11)2 | A,B | — | — |
| 29 | H | CO(CH2)3CH(C6H11)2 | A,B | — | — |
| 30 | H | CO(CH2)4CH(C6H11)2 | A,B | — | — |
| 31 | H | CO(CH2)5CH(C6H11)2 | A,B | — | — |
| 32 | H | CO(CH2)6CH(C6H11)2 | A,B | — | — |

Appendix to TABLE I

[a]70%; oil; MS m/e 275 (M+); $^1$H NMR (CDCl$_3$): imidazole H: δ 7.60 and 6.75 (s, 1H); piperidine H: complex, δ 4.65 (d, 2H), 3.90 (d, 2H), 3.10 (m, 3H), 2.10 (m, 2H); cyclohexyl acetyl H: δ 1.50 (m, 11H), 2.80 (m, 2H).

[b]67%; oil; MS: m/e 267 (M+); $^1$H NMR (CDCl$_3$): imidazole H: δ 7.50 and 6.60 (s, 1H); piperidine H: complex, δ 3.90 (d, 2H), 2.80 (m, 3H), 2.55 (m, 2H), 1.80 (m, 2H); phenyl acetyl H: δ 7.10 (m, 5H), 1.50 (m, 2H).

[c]71%; oil; MS: m/e 297 (M+); $^1$H NMR (CDCl$_3$): imidazole H: δ 7.80 and 6.70 (s, 1H); piperidine H: complex, δ 4.60 (d, 2H), 3.80 (d, 2H), 3.10 (m, 3H), 1.80 (d, 2H); phenyl propyl H: δ 7.20 (m, 5H), 2,65 (m, 2H), 235 (m, 2H), 2.10 (m, 2H).

[d]74%; oil; MS: m/e 289 (M+); $^1$H NMR (CDCl$_3$): imidazole H: δ 7.70 and 6.80 (s, 1H); piperidine H: complex, δ 4.60 (d, 2H), 3.85 (d, 2H), 3.10 (m, 3H), 1.90 (m, 2H); cyclohexyl ethyl H: δ 1.10 (m, 11H), 2.00 (br, 2H), 2.20 (m, 2H).

[e]75%; oil; MS: m/e 283 (M+); $^1$H NMR (CDCl$_3$): imidazole H: δ 7.60 and 6.70 (s, 1H); piperidine H: complex, δ 4.60 (d, 2H), 3.90 (d, 2H), 3.10 (m, 3H), 1.80 (m, 2H); phenyl ethyl H: δ 7.30 (m, 5H), 2.10 (br, 2H), 1.50 (m, 2H).

[f]69%; M.P.: 151° C.; MS: m/e 327 (M+); $^1$H NMR (CDCl$_3$): imidazole H: δ 7.65 and 6.80 (s, 1H); piperidine H: complex, δ 4.70 (d, 2H), 4.50 (d, 2H), 3.60 (m, 1H), 2.80 (m, 2H), 2.10 (m, 2H); adamantyl acetyl H: δ 1.80 (m, 12H), 3.10 (m, 2H), 4.05 (m, 1H).

[g]62%; M.P.: 148° C. (decomposed); MS: m/e 357 (M+); $^1$H NMR (CDCl$_3$): imidazole H: δ 7.60 and 6.85 (s, 1H); piperidine H: complex, δ 4.50 (d, 2H), 4.05 (m, 3H), 3.40 (d, 2H), 2.10 (m, 2H); dicyclohexyl acetyl H: δ 1.50 (m, 22H), 2.50 (m, 1H).

[h]64%; oil; MS: m/e 281 (M+); $^1$H NMR (CDCl$_3$): imidazole H: δ 7.75 and 6.60 (s, 1H); piperidine H: complex, δ 4.70 (d, 2H), 4.20 (m, 3H), 2.80 (m, 2H), 2.10 (d, 2H); phenyl vinyl H: δ 7.40 (m, 5H), 6.50 (m, 2H).

[i]62%; oil; MS m/e 351 (M+); $^1$H NMR (CDCl$_3$): imidazole H: δ 7.50 and 6.40 (s, 1H); piperidine H: complex, δ 4.60 (d, 2H) 4.10 (m, 3H), 2.80 (d, 2H), 1.80 (m, 2H); phenyl cyclohexyl acetyl H: δ 7.20 (m, 5H), 1.80 (m, 11H), 3.70 (m, 1H).

[j]yield: 72%; M.P.: 136° C.; MS:m/e 304 (M+); $^1$H NMR (CDCl$_3$): imidazole H: δ 7.70 and 6.80 (s, 1H); piperidine H: complex, δ 4.60 (d, 2H), 4.00 (m, 2H), 3.60 (m, 3H), 1.88 (m, 2H); cyclohexyl propyl H; complex, δ 1.20 (m, 17H).

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

What is claimed is:

1. A process for the preparation of a compound of Formula (3):

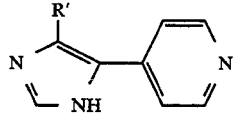

wherein R' is H or $C_1-C_4$ alkyl; which comprises:
(1) reacting a compound of the Formula (1)

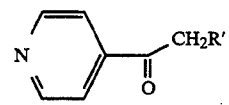

wherein R' is H or $C_1-C_4$ alkyl; with
an activating reagent which is capable of removing a hydrogen atom from the α-methyl group of (1) and replacing that hydrogen with a halogen, hydroxy or amino function in a suitable solvent to produce an activated compound of the Formula (2a)

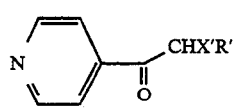

wherein X' is halogen, hydroxy or amino and R'is H or $C_1-C_4$ alkyl; and
(2) reacting a compound of the Formula (2a) with a compound of the Formula

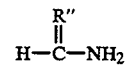

where R" is NH or O at an elevated temperature to yield a compound of the Formula (3).

2. A process according to claim 1 where the activating reagent in step (1) is selected from the group consisting of (1) bromine or chlorine, (2) molybdenum peroxide and (3) bromine or chlorine followed by hexamethylenetetramine.

3. A process according to claim 1 wherein R' in step (1) is H or methyl.

4. A process according to claim 1 wherein R" in step (2) is NH.

5. A process according to claim 1 wherein R" in step (2) is O.

6. A process according to claim 1 wherein X' in step (1) is a halogen.

7. A process according to claim 6 wherein X' in step (1) is bromine.

8. A process according to claim 1 wherein said suitable solvent in step (1) is acetic acid.

9. A process according to claim 1 wherein said elevated temperature in step (2) is from about 50° to about 300° C.

* * * * *